United States Patent [19]

Thompson

[11] Patent Number: 5,172,580
[45] Date of Patent: Dec. 22, 1992

[54] NON-DESTRUCTIVE DETERMINATION OF SURFACE COLD WORK DUE TO A SHOT PEENING OPERATION

[75] Inventor: Robert A. Thompson, Quaker Street, N.Y.

[73] Assignee: General Electric Company, Schenectady, N.Y.

[21] Appl. No.: 844,025

[22] Filed: Mar. 2, 1992

[51] Int. Cl.⁵ ............................................. B24C 1/10
[52] U.S. Cl. ................................... 72/53; 72/53; 51/319; 29/90.1
[58] Field of Search ................ 72/53, 9, 10; 29/90.1; 51/319, 320; 364/474.15, 474.16, 474.17, 474.37

[56] References Cited

U.S. PATENT DOCUMENTS

| | | | |
|---|---|---|---|
| 4,687,556 | 8/1987 | Sutton et al. | 72/53 |
| 4,693,102 | 9/1987 | Amy et al. | 72/53 |
| 4,873,855 | 10/1989 | Thompson | 72/53 |
| 5,003,805 | 4/1991 | Thompson | 72/53 |

Primary Examiner—David Jones
Attorney, Agent, or Firm—James R. McDaniel; Paul R. Webb, II

[57] ABSTRACT

This invention relates to a method for directly measuring the amount of surface cold work due to a surface treatment operation. Such methods of this type, generally, allow the surface cold work created by a shot peening operation to be directly measured without having to destruct the substrate.

3 Claims, 4 Drawing Sheets

NON-DESTRUCTIVE DETERMINATION OF SURFACE COLD WORK DUE TO A SHOT PEENING OPERATION

BACKGROUND OF THE INVENTION

1. Field of the Invention

This invention relates to a method for directly measuring the amount of surface cold work due to a surface treatment operation. Such methods of this type, generally, allow the surface cold work created by a shot peening operation to be directly measured without having to destruct the substrate.

2. Description of the Related Art

Plastic strain is the mechanism whereby the surface is put into a state of compressive residual stress and it can further increase dislocation density, these being the key life enhancing benefits of the peening process. However, if the total cold work during peening exceeds the ductility limit of the material surface, embrittlement may result which can enhance crack initiation and growth. Excessive cold work is, therefore, an important damage mechanism for the process. Means to nondestructively measure the amount of cold work due to peening is critical for guaranteeing the life of high performance mechanical components.

Cold work is the result of the two shot peening variables, intensity and coverage. Intensity, or the energy imparted to the surface by individual impacts effects the amount of plastic strain induced in the surface by each shot strike. Coverage, on the other hand, is a measure of the number of times each element of the surface is cold worked during a shot peening operation. A coverage of 200% indicates that on average each point of the surface has been struck twice during the peening operation.

Methods to measure intensity from profilometer traces of a shot peened surface are disclosed in U.S. Pat. No. 5,003,805, entitled "Method and System for Monitoring Shot Peening" to R. A. Thompson and assigned to the same assignee as the present invention and U.S. patent application Ser. Nos. 646,957 and 650,828 entitled "Non-Destructive Monitoring of Surfaces by 3-D Profilometry" and "Quality Assurance of Surface Treatments by Analysis of Surface Line Traces", respectively, both to Thompson et al. and assigned to the same assignee as the present invention. Other methods to measure intensity would also apply. Similarly, U.S. patent application Ser. Nos. 764,034 and 850,732, respectively, entitled "Measurement of the Shot Peening Coverage by Automated Analysis of Peened Surface Line Traces" and "Measurement of Shot Peening Coverage by Impact Dent Characterization", both to Thompson et al. and assigned to the same assignee as the present invention, describe ways to use surface profile data to measure coverage, or the number of strikes the surface experiences during a peening operation.

While these methods have met with a modicum of success, none of these systems employ both intensity and coverage information to determine cold work, and the extent to which a peened surface is approaching embrittlement and the risk of fatigue or stress corrosion cracking failure. Therefore, a more advantageous system, then, would be presented if such amounts of embrittlement and fatigue could be determined.

Equally important to the shot peening of complex surfaces is the fact that the number and intensity of strikes may vary with part shape at different locations as the sprayed shot stream passes over them. At locations where excessive strikes occur, excessive cold work may lead to embrittlement and in increased risk in failure. This effect may be most severe, in fact, in critical, high stress regions such as fillets and corners, where ricochets can greatly increase the number of bombardments and impacts on sharp corners can greatly increase local intensity.

For this reason, conventional methods of determining intensity and coverage by Almen strips and die tracers may fall short. Similarly, NDE methods of measuring cold work take on added importance. Even advanced computational methods for calculating cold work from intensity and coverage models of complex geometrical regions require NDE verification before they can be used with confidence. Nevertheless, further reductions in NDE vertification would be advantageous.

It is apparent from the above that there exists a need in the art for a system that measures surface cold work due to a shot peening operation, and which measures the surface cold work in a non-destructive manner, but which at the same time is capable of determining the extent to which a peened surface is approaching embrittlement and the risk of fatigue or stress corrosion cracking failure. It is a purpose of this invention to fulfill this and other needs in the art in a manner more apparent to the skilled artisan once given the following disclosure.

SUMMARY OF THE INVENTION

Generally speaking, this invention fulfills these needs by providing a method for a non-destructive determination of surface cold work due to a shot peening operation including a substrate having a first side which has been surface treated, comprising the steps of obtaining profile data of said first side such that said profile data is being obtained in a non-destructive and direct manner, selecting a dent in said first side to be analyzed, calculating a plastic strain for said dent, determining a percent of coverage of said surface treatment, calculating an actual total surface cold work, and adjusting, if needed, the peening operation so that the actual total surface cold work of a subsequently peened surfaces will be more in conformance with a predetermined desired total surface cold work.

In certain preferred embodiments, the plastic strain ($\epsilon p$) is calculated according to the equation (1):

$$\epsilon p = d^2/8D^2 \qquad (1)$$

where d is the surface diameter of the dent and D is the generating diameter of the crater (ball diameter). Also, the actual amount of total surface cold work in percent strain is calculated according to Equation (2):

$$\text{Cold work} = \epsilon p N \qquad (2)$$

where N is the percent coverage.

In another further preferred embodiment, the actual amount of surface cold work due to a shot peening operation can be accurately determined in a non-destructive and direct manner.

The preferred system, according to the present invention, offers the following advantages: ease of use; excellent surface cold work determination characteristics; good stability; good durability; and good economy. In fact, in many of the preferred embodiments, these factors of ease of use and cold work determination characteristics are optimized to an extent considerably higher than heretofore achieved in prior, known surface treatment evaluation systems.

BRIEF DESCRIPTION OF THE DRAWINGS

The above and other features of the present invention which will become more apparent as the description proceeds are best understood by considering the following detailed description in conjunction with the accompanying drawings wherein like characters represent like parts throughout the several views and in which.

DETAILED DESCRIPTION OF THE INVENTION

The total cold work at a point equals the plastic strain (intensity) for an individual impact times the number of impacts at that point (coverage). Cold work is additive. Thus, in cases where multiple passes at different intensities (i.e. incident angles, etc.) are a part of the total peening process, each intensity can be multiplied by its associated coverage and the results added to give the total cold work. Ricochet induced cold work can be treated in a similar way. Methods to measure intensity and coverage from profilometer traces of shot peened surfaces were covered in the above reference prior art and so this description needs only to clarify how they are combined to determine surface cold work, and the extent to which the peened surface is approaching embrittlement and the risk of failure.

Consider first the contribution of intensity. Intensity in simplest terms is the depth of the compressive or plastically reworked surface layer. This depth very nearly equals the diameter of the dimples produced by individual shot strikes. This is described in U.S. Pat. No. 5,003,805 which describes a basic way to measure dimple diameter. From the measured dimple diameter information and a knowledge of the shot diameter the cold work attributable to a single shot strike can be worked out as follows.

Figure 1:
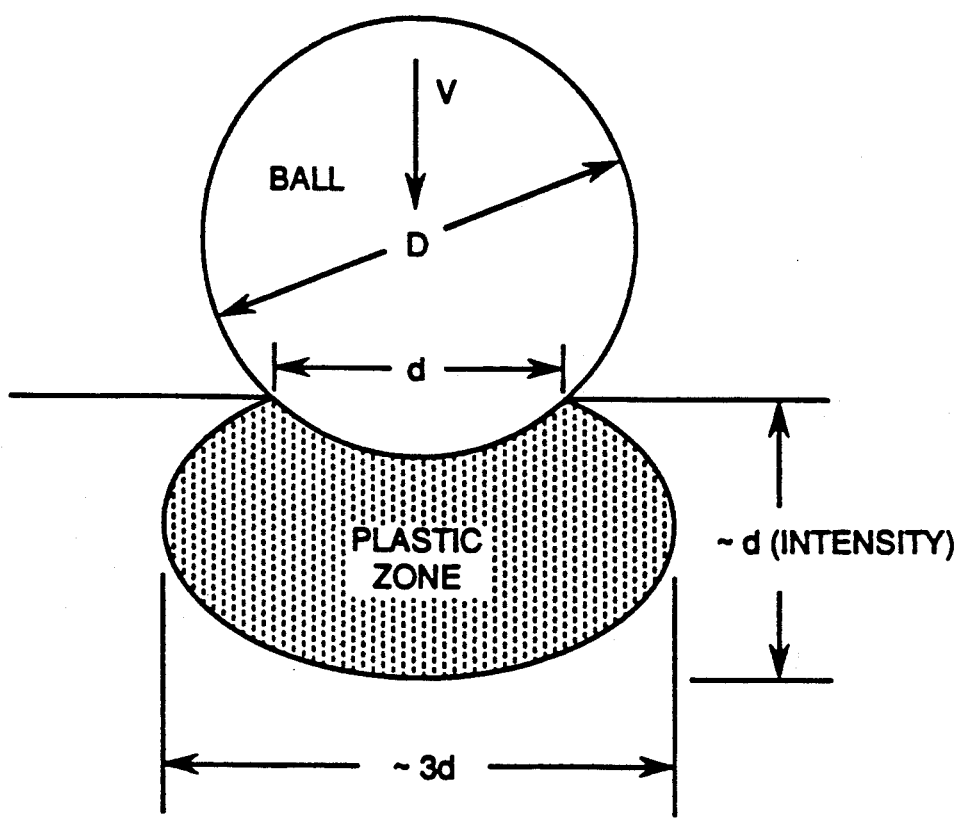
FIG. 1 is a schematic illustration of shot/workpiece impact.

With respect to FIG. 1, a nominally flat surface has been struck by a rigid ball of diameter, D, leaving the spherical cavity of diameter, d, at the surface. The elements of the struck surface had to stretch to accommodate the dimple so that a flat circular region of area, A, stretched into a spherical cavity of surface area $A + \Delta A$, characterized by the surface diameter, d, and the generating diameter, D. To accommodate this change it can be shown that the generating lines for the surface underwent an average unrecovered tensile strain of:

$$\epsilon p = \Delta l/l = \Delta A/2A \quad (3)$$

The calculation of $\Delta A/A$ is as follows:

$$A = \pi d^2/4 \quad (4)$$

$$\Delta A/A = (A + \Delta A)/A - 1 \quad (5)$$

$$A + \Delta A = .5\pi D^2 (1 - \sqrt{1 - d^2/D^2}) \quad (6)$$

By dividing equation (4) into equation (6) it can be shown that:

$$\Delta A/A = \frac{2D^2}{d^2}(1 - \sqrt{1 - d^2/D^2}) - 1 = \quad (7)$$

$$\frac{d^2}{4D^2} + \frac{d^4}{8D^4} + \frac{5d^6}{64D^6} + \ldots$$

Noting that under ordinary conditions only the first term on the right hand side of equation (7) is significant, equations (3) and (7) lead to a plastic strain for an individual impacts of:

$$\epsilon_p = d^2/8D^2 \quad (1)$$

Figure 2:
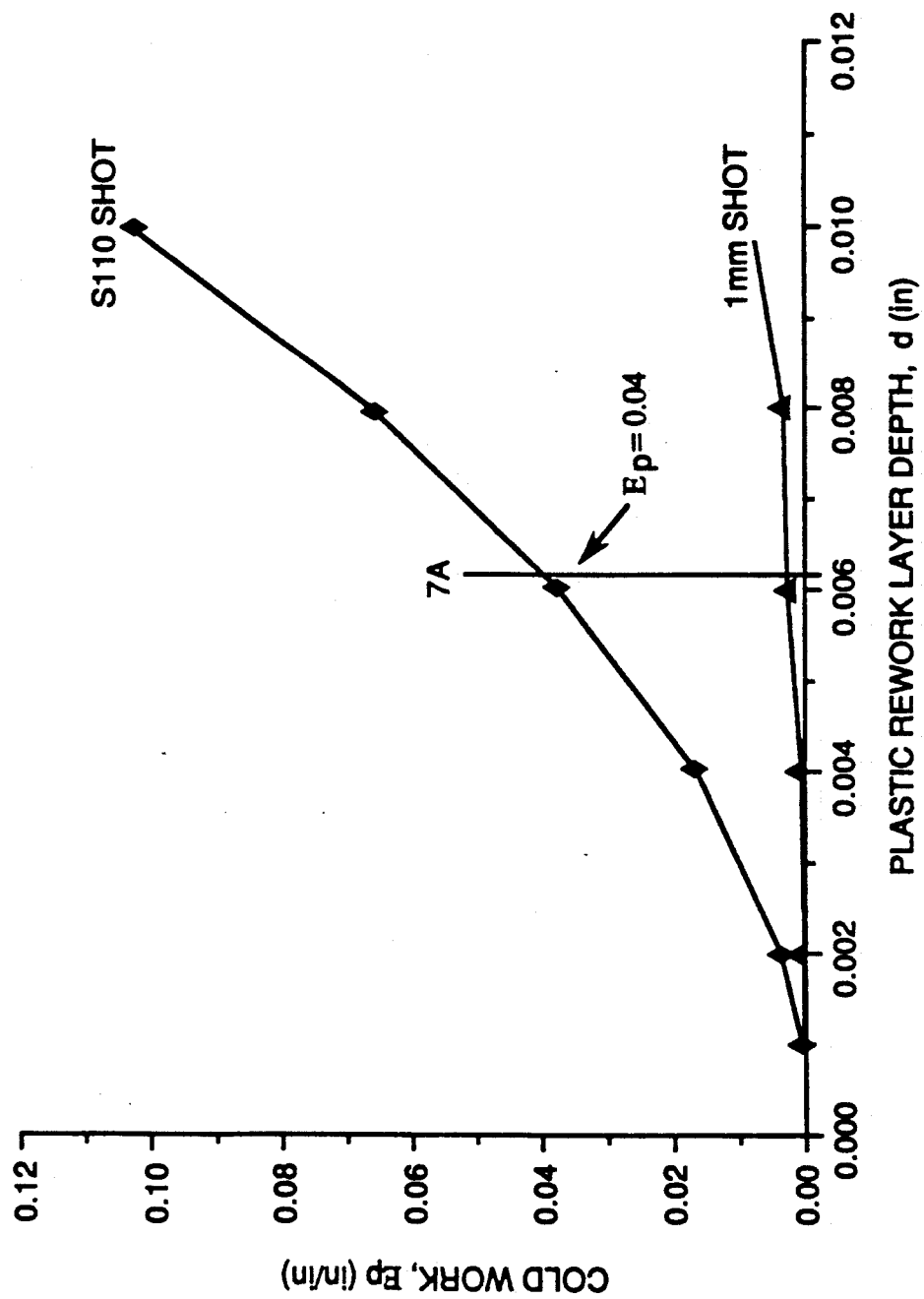
FIG. 2 is a graphical representation of single impact intensity/shot diameter effects with plastic strain ($\epsilon p$) in (in/in) versus plastic rework layer depth (d) in (in)

In equation (1), the quantity, d, is the intensity as described in the above referenced prior art. The shot diameter is D, so that by measuring the intensity and knowing the shot size, the cold work for a single impact can be determined from equation (1). FIG. 2 shows how this quantity varies with intensity (plastic rework layer depth, d) for two typical sizes of shot (note S110 shot is nominally 0.011" in diameter).

Next, the effect of coverage can be considered. As stated above, coverage indicates the average amount of each element of surface area as struck during a peening operation. Thus 200% coverage indicate that each area element was cold worked twice during the operation. In this case, the total strain would be two times the strain given by equation (1). This idea can be generalized by defining as the percent coverage the quantity N and multiplying N times equation (1). Thus, the total cold work during a peening operation can be described mathematically as $$\text{Cold Work} = d^2 N/8D^2 \text{percent} \quad (2)$$

Note here that cold work is described as a percent instead of as a decimal as it was in equation (1). This is because it is convenient to describe N as a percent. Thus, for example, if $\epsilon_p = 0.01$ and the coverage is 100%, the resultant cold work would conveniently be described as Cold Work $= 0.01 \times 100 = 1\%$.

Figure 3:
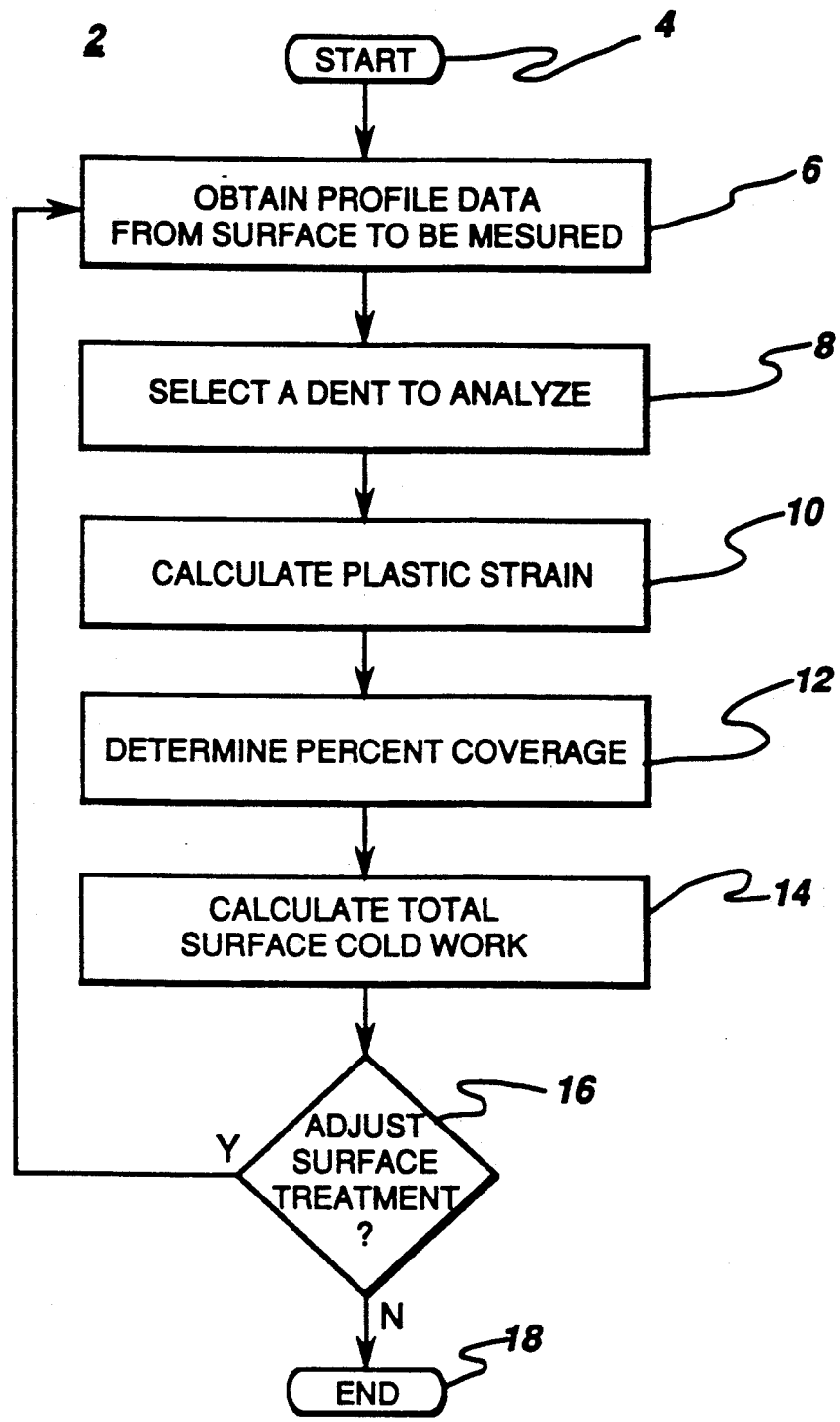
FIG. 3 is a flowchart illustrating a sequence of method steps, in accordance with the present invention.

To calculate the total surface cold work, after a substrate surface has been peened, a system user initiates the process which is briefly illustrated as a flow diagram 2 in FIG. 3. The system user may, for example, be a human or a computer including a computer-controlled robotic unit. Specifically referring to flowchart 2, after the process has been initiated as indicated at a start block 4, the system user obtains a profile of the workpiece surface to be measured as indicated at block 6. The profile may be obtained by using a profilometer such as a commercially available profilometer such as a commercially available profilometer known as a Taylor Hopson "Form Taylsurf", available from Rank Taylor Hopson, Limited (British Company). Other profilometers, for example, stylus or non-contacting type such as that of the Wyko Corporation, with suitable sensitivity could provide the necessary profile data. From the profiled data, the system user then selects a dent to analyze as shown at block 8. After the dent has been selected, the plastic strain ($\epsilon p$) is calculated according to equation (1) as shown at block 10. Once the plastic strain has been calculated, the system user determines the percent of coverage as shown at block 14. After the percent coverage has been determined, the total amount of surface cold work (cold work) is calculated according to equation (2) as shown at block 14. The total amount of surface cold work is compared with a predetermined, desired amount of surface cold work to determine, if any, what adjustments should be made to the surface treatment operation as indicated at blocks 16 and 18. FIG. 3 demonstrates the principle of cold work determination. Other methods of measuring intensity and coverage such as those described as prior art, would apply as well.

Figure 4:
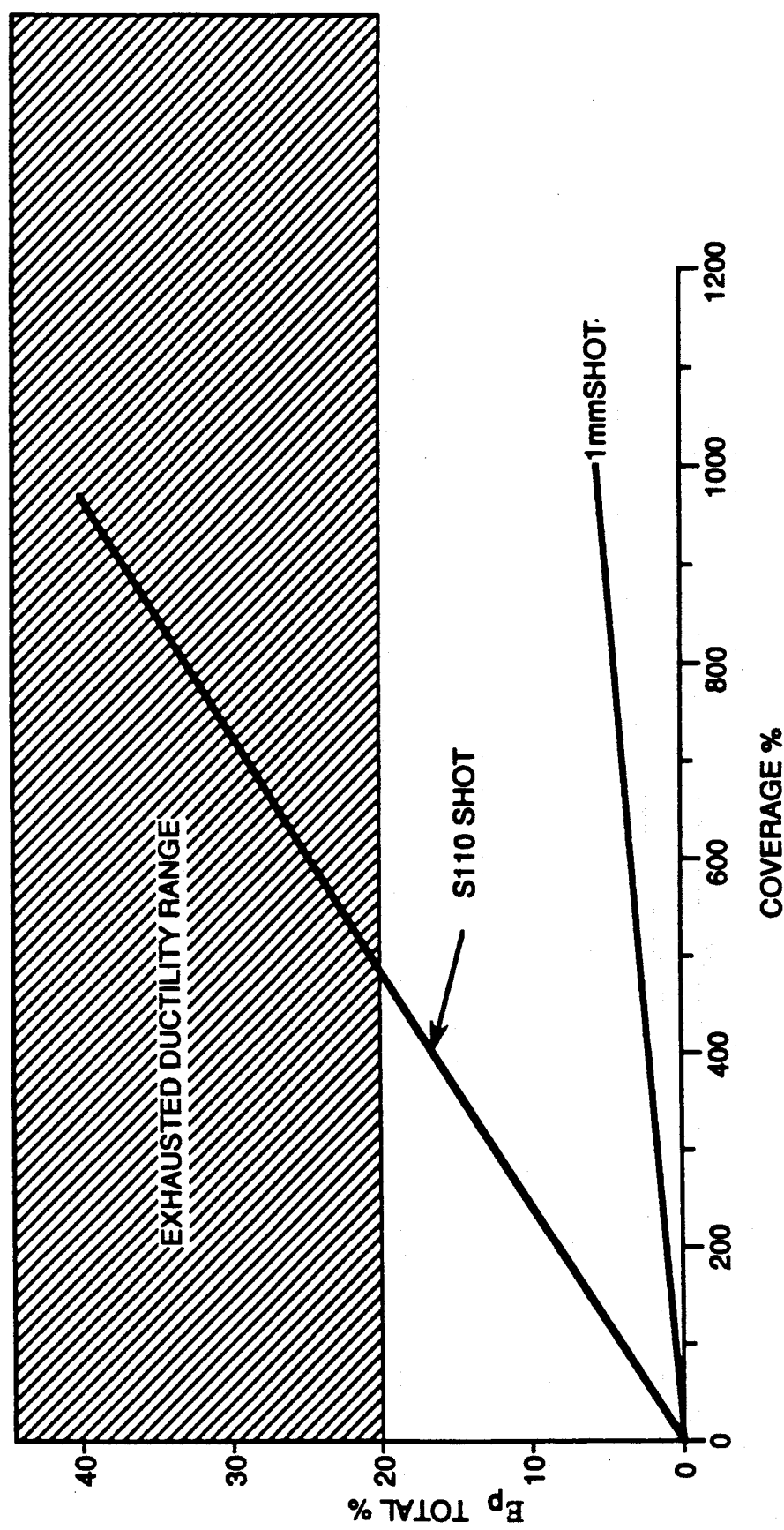
FIG. 4 is a graphical representation of total surface cold work with total $\epsilon p$ (%) plotted against coverage (%).

In general, the ductility limit of aircraft engine superalloy materials is around 20 to 40%. When this limit is exceeded embrittlement and damage can occur. FIG. 4 shows how the limit is approached for a 7A intensity peening (d=0.0061 inches) as a function of coverage for two different shot diameters, D, as indicated. It is clear that the approach to trouble for S-110 (0.011 inch diameter) shot is about 500% coverage, a value not uncommon in complex peening situations. This fact emphasizes the importance of this disclosure and shows how independent NDE measurements of intensity and coverage can be used synergistically to determine the very important peening parameter, cold work.

Once given the above disclosure, many other features, modifications or improvements will become apparent to the skilled artisan. Such features, modifications or improvements are, therefore, considered to be apart of this invention, the scope of which is to be determined by the following claims.

What is claimed is:

1. A method for a non-destructive determination of surface cold work due to a shot peening operation including a substrate having a side which has been surface treated, said method comprising the steps of:
   obtaining profile data of said surface treated side in a non-destructive and direct manner, said profile data being indicative of dents caused by said shot peening operation;
   selecting a dent from said profile data to be analyzed;
   calculating a plastic strain for said dent;
   determining a percent of coverage of said surface treated side;
   calculating an actual total surface cold work; and
   adjusting, if needed, the peening operation so that the actual total surface cold work of a subsequently formed dent will be more in conformance with a predetermined desired total surface cold work.

2. The method, according to claim 1, wherein said step of calculating said plastic strain is further comprised of the step of:

$$\text{calculating } \epsilon_p = d^2/8D^2$$

wherein:
$\epsilon_p$ = plastic strain for an individual impact
d = dent diameter, and
D = shot diameter.

3. The method, according to claim 1, wherein said step of calculating said actual total surface cold work is further comprised of the step of:
   calculating $$\text{Cold Work} = \epsilon_p N$$

wherein:
Cold Work = the actual total percent surface cold work
$\epsilon_p$ = plastic strain for an individual impact; and
N = percent of coverage.

* * * * *